US007217513B2

(12) United States Patent
Parameswaran et al.

(10) Patent No.: US 7,217,513 B2
(45) Date of Patent: May 15, 2007

(54) APPARATUS AND METHOD FOR ISOLATING A NUCLEIC ACID FROM A SAMPLE

(75) Inventors: Lalitha Parameswaran, Burlington, MA (US); Albert Young, Fishkill, NY (US); Laura T. Bortolin, Concord, MA (US); Mark A. Hollis, Concord, MA (US); James Harper, Boston, MA (US); Johanna Bobrow, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 481 days.

(21) Appl. No.: 10/193,742

(22) Filed: Jul. 10, 2002

(65) Prior Publication Data

US 2003/0129614 A1 Jul. 10, 2003

Related U.S. Application Data

(60) Provisional application No. 60/304,608, filed on Jul. 10, 2001.

(51) Int. Cl.
*C12Q 1/68* (2006.01)
(52) U.S. Cl. ........................................................ 435/6
(58) Field of Classification Search .................... 435/6; 436/527; 568/324
See application file for complete search history.

(56) References Cited

U.S. PATENT DOCUMENTS

| | | |
|---|---|---|
| 5,234,809 A | 8/1993 | Boom et al. |
| 5,496,562 A | 3/1996 | Burgoyne |
| 5,660,984 A | 8/1997 | Davis et al. |
| 5,707,850 A | 1/1998 | Cole |
| 5,756,126 A | 5/1998 | Burgoyne |
| 5,804,684 A * | 9/1998 | Su .............................. 536/25.4 |
| 5,807,527 A | 9/1998 | Burgoyne |
| 5,840,169 A | 11/1998 | Andersen |
| 5,863,801 A | 1/1999 | Southgate et al. |
| 5,910,246 A * | 6/1999 | Walter et al. ................ 210/232 |
| 5,939,259 A * | 8/1999 | Harvey et al. .................. 435/6 |
| 5,972,386 A | 10/1999 | Burgoyne |
| 5,976,572 A | 11/1999 | Burgoyne |
| 5,985,327 A | 11/1999 | Burgoyne |
| 6,037,465 A | 3/2000 | Hillebrand et al. |
| 6,168,922 B1 | 1/2001 | Harvey et al. |
| 6,218,176 B1 | 4/2001 | Berthold et al. |
| 6,264,814 B1 | 7/2001 | Lange |
| 6,374,684 B1 | 4/2002 | Dority |
| 6,428,962 B1 | 8/2002 | Naegele |
| 6,431,476 B1 | 8/2002 | Taylor et al. |
| 6,440,725 B1 | 8/2002 | Pourahmadi et al. |
| 6,673,631 B1 * | 1/2004 | Tereba et al. ................ 436/526 |

2002/0042125 A1 4/2002 Peterson et al.

FOREIGN PATENT DOCUMENTS

WO WO 9913976 A1 * 3/1999

OTHER PUBLICATIONS

Brush, "PCR on the Run," The Scientist, Jun. 26, 2000, vol. 14, No. 13, pp. 1-5.*
S.N.A.P. MidiPrep Kit, Invitrogen Instruction Manual, Catalog No. K1910-01.*
Smail et al., "Rapid, Cost-effective Gene Mutation Screening for Carnitine Palmitoyltransferase II Deficiency Using Whole Blood on Filter Paper," Clinical Chemistry, 1999, vol. 45, No. 11, pp. 2035-2038.*
Fiscus et al., "Quantitation of Human Immunodeficiency Virus Type 1 RNA in Plasma by Using Blood Dried on Filter Paper," Journal of Clinical Microbiology, Jan. 1998, vol. 36, No. 1, pp. 258-260.*
Chandler et al., "Automated nucleic acid isolation and purification from soil extracts using renewable affinity microcolumns in a sequential injection system," Talanta 1999, vol. 49, pp. 969-983.*
Itoh et al., "Automated Filtration-Based High-Throughput Plasmid Preparation System," Genome Research, 1999, No. 9, pp. 463-470.*
Andreotti, P., "Portable Swab Sample Processor (SSP) and Analyzer for Rapid Detection of Biothreat Agents," *Defense Advanced Research Projects Agency, Tissue Based Biosensors, Advanced Diagnostics, Activity Detection Technologies Principle Investigator Conference 2002*, DARPA, Miami, Florida, Feb. 18-21, 2002.
Cepheid News; "Cepheid Collaborates on Major U.S. Postal Contract for Bio-threat Detection—Pilot Program to Employ GeneXpert® DNA-Detection System," at http://www.cepheid.com/pages/press/020513.html, Sunnyvale, CA, May 13, 2002.
Levy, S., "A Fully Automated High-Throughput Nucleic Acid Purification System Using Silica Coated Magnetic Bead Technology," *Laboratory Robotics Interest Group, New England Chapter, Poster Session, Mar. 26, 2002*, from http://www.lab-robotics.org/New_England/Posters/LRIG—New%20England%20Posters%20March%2026,2002.pdf.

(Continued)

*Primary Examiner*—Young J. Kim
(74) *Attorney, Agent, or Firm*—Hamilton, Brook, Smith & Reynolds, P.C.

(57) ABSTRACT

A method for preparing a nucleic acid component of a sample for amplification includes contacting the sample with a porous support that deactivates a nucleic acid amplification inhibitor component of the sample and directing a fluid through the porous support, whereby the nucleic acid component of the sample is directed through at least a portion of the porous support and is separated from the support, thereby preparing the nucleic acid component for amplification. The method can be conducted in an apparatus that includes a porous support having a component that deactivates a nucleic acid amplification inhibitor component of a sample contacting the porous support and a housing having an opening and defining an interior, said interior being in fluid communication with the porous support, whereby at least a portion of a fluid directed through the opening is directed through at least a portion of the porous support and separates at least a portion of a nucleic acid component of a sample contacting the porous support from the support, thereby preparing the nucleic acid component for amplification.

64 Claims, 13 Drawing Sheets

OTHER PUBLICATIONS

Parameswaran, L., "Development of Recovery Techniques for Organisms and Nucleic Acids from Complex Samples", *Third Annual Biodetection Technologies 2003 International Symposium*, from http://www.knowledgepress.com/event/12111105.htm.

Schmidt, J.C., "A Portable Biodetection System Incorporating Semi-Automated Sample Preparation," *Detection Technologies—The Next Generation in Identification and Analysis*, Arlington, Virginia, Dec. 5-6, 2002, http://www.knowledgepress.com/events/7191716.htm.

Taylor, Michael T., et al., "Lysing Baterial Spores by Sonication through a Flexible Interface in a Microfluidic System," *Anal. Chem.*, 73:492-496 (2001).

Tu, Shu-I, et al., "Applications of Time-Resolved Fluoroimmunoassay to Detect Magnetic Bead Captured *Escherichia Coli* 0157:H7," *Journal of Rapid Methods and Automation in Microbiology*, 9:71-84 (2001).

Cepheid Technology; "Fluidic Systems" at http://www.cepheid.com, Jun. 5, 2002.

"How GeneXpert Automates Sample Preparation," at http://media.corporate-ir.net, Jun. 5, 2002.

"Cepheid Granted U.S. Patent Covering GeneXpert (R) Cartridge," at http://biz.yahoo.com, Jun. 5, 2002.

Xtrana: Products: Nucleic Acid Testing; "SCIP: Self Contained Integrated Particle," http://www.xtrana.com, Jun. 5, 2002.

* cited by examiner

APPARATUS AND METHOD FOR ISOLATING A NUCLEIC ACID FROM A SAMPLE

RELATED APPLICATIONS

This application claims the benefit of U.S. Provisional Application No. 60/304,608, filed Jul. 10, 2001, the entire teachings of which are incorporated herein by reference.

GOVERNMENT SUPPORT

The invention was supported, in whole or in part, by Lincoln Contract Number F19628-95-C-0002 from Defense Directorate of Research and Engineering. The Government has certain rights in the invention.

BACKGROUND OF THE INVENTION

Nucleic acids generally are analyzed by polymerase-chain-reaction (PCR) procedures. The presence of PCR inhibitors, such as often encountered in samples collected for medical diagnosis, during forensic investigations or in defense-related applications, hinders PCR-amplification.

It is difficult, for example, to extract amplifiable DNA from soil or slurry raw samples, in particular, from samples that include clays or other soils that have high organic content.

Conventional techniques for extracting amplifiable nucleic acids from samples generally are complicated, labor-intensive, and require laboratory facilities and equipment. Many existing protocols also require toxic reagents, such as phenol and chloroform.

One material developed for DNA isolation, in particular in conjunction with handling blood samples, is a chemically treated cotton matrix available from Schleicher and Schuell, Inc., of Keene, N.H., under the tradename of IsoCode®. IsoCode®-based protocols adapted to handle raw samples, such as described above, still require laboratory equipment, external reagents and entail numerous steps (including two oven drying cycles). Moreover, as with other approaches, the samples are susceptible to sample contamination.

Therefore, a need exists for a method for preparing a nucleic acid component of a sample for amplification that is faster, less complicated and less labor-intensive than existing protocols. A need also exists for an apparatus for conducting such a method. In particular, there exists a need for a portable, self-contained device, suitable for field use, that can be employed for preparing a nucleic acid component of a sample for amplification and can be used for analyzing, storing or archiving the resulting nucleic acid component.

SUMMARY OF THE INVENTION

The invention generally is related to a method and apparatus for preparing a nucleic acid component of a sample for amplification.

The method includes the steps of contacting the sample with a porous support that deactivates a nucleic acid amplification inhibitor component of the sample and directing a fluid through the porous support, whereby the nucleic acid component of the sample is directed through at least a portion of the porous support and is separated from the porous support, thereby preparing the nucleic acid component for amplification.

For example, the porous support includes an agent that deactivates the nucleic acid inhibitor component of the sample, such as, for instance a chaotropic salt. Preferably the agent also kills cell or spores, deactivates DNases or RNases or lyses cells or spores to release nucleic acid.

An apparatus for preparing a nucleic acid component of a sample for amplification includes a porous support having a component that deactivates a nucleic acid amplification inhibitor component of a sample contacting the porous support and a housing having an opening and defining an interior, said interior being in fluid communication with the porous support, whereby at least a portion of a fluid directed through the opening is directed through at least a portion of the porous support and separates at least a portion of a nucleic acid component of a sample contacting the porous support from the support, thereby preparing the nucleic acid component for amplification.

The invention has numerous advantages. For example, the invention can be used with solid, semi-solid, liquid or aerosol samples. By employing the invention, a nucleic acid component in a raw sample can be prepared for amplification in a reduced number of steps that can be completed in minutes. Forced flow-through of the elution fluid is faster than diffusive movement through a porous substrate that deactivates a nucleic acid amplification inhibitor and obviates or minimizes the need for heat. Addition of external reagents also is reduced or entirely eliminated, lessening the potential for sample contamination. Furthermore, the method of the invention can be conducted using water (or water and buffer compounds) as the only reagent. By employing the apparatus of the invention, samples can be collected and prepared in the field, with minimum transport considerations and the collection and preparation steps can be conducted using heavy gloves and protective gear. The samples prepared can be archived and/or can be amplified using standard equipment, as known in the arts. The apparatus of the invention is lightweight, compact, can be subjected to decontamination of its outer surfaces and can be manufactured economically for disposable use.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention. All parts and percentages are by weight unless otherwise indicated.

DETAILED DESCRIPTION OF THE INVENTION

Figure 1:
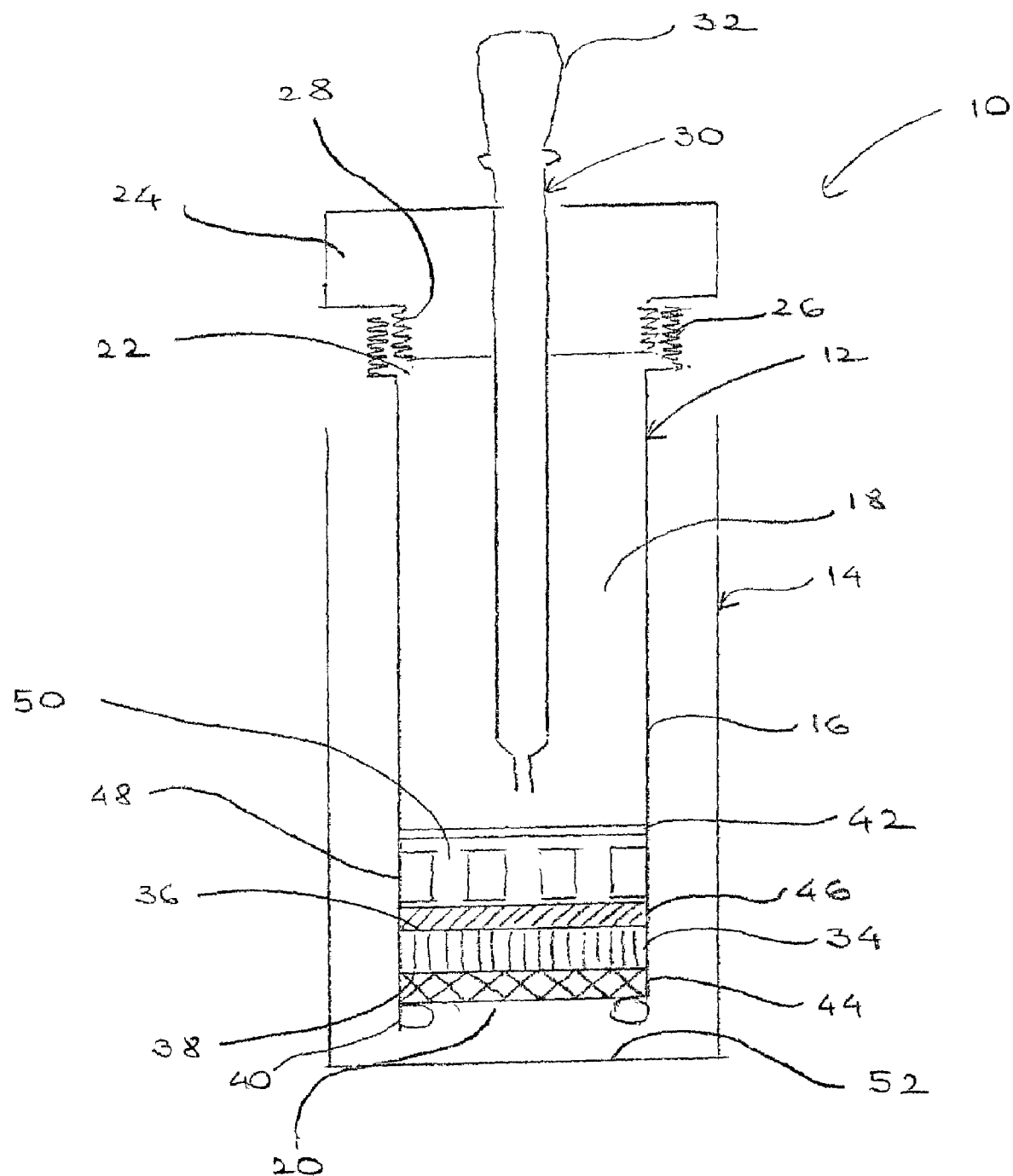
FIG. 1 is a longitudinal cross sectional view of an embodiment of the apparatus of the invention which can be employed to conduct the method of the invention.

A description of preferred embodiments of the invention follows.

The invention generally is related to a method and apparatus for preparing a nucleic acid component of a sample for amplification.

The method of the invention includes the steps of contacting the sample with a porous support that deactivates a nucleic acid amplification inhibitor component of the sample and directing a fluid through the porous support, whereby the nucleic acid component of the sample is directed through at least a portion of the porous support and is separated from the support, thereby preparing the nucleic acid component for amplification.

The method of the invention is suitable for handling samples that include a nucleic acid component. As used herein, the term nucleic acid includes poly or oligo nucleotides. Examples of nucleic acids include, but are not limited to, DNA, RNA, fragments thereof, isotopically tagged nucleic acids or any combinations thereof.

The sample also includes a nucleic acid amplification inhibitor component. The inhibitor can be a PCR inhibitor or a compound or material that is capable of damaging nucleic acids. Examples include, but are not limited to, hemoglobin, humic acid, fulvic acid, divalent cations, chelating molecules, enzymes, proteins and others. One or more nucleic acid amplification inhibitors can be present in the sample.

The method of the invention is particularly useful for handling samples that are collected during forensic investigations, defense-related applications or in the medical field. Such samples can include plant or animal tissue, blood, bodily fluids, feces, saliva, urine, buccal swabs, bacteria, microorganisms, pathogens, spores, fungi, viruses, food, cells, soils, e.g., clays, combinations thereof, and many others.

The sample can be in solid, liquid, slurry or gaseous form.

The sample is contacted with a porous support. For example, liquid samples are brought to wet the porous support by dispensing the sample onto the porous support or by immersing the porous support in the sample.

Solid samples can be contacted with the porous support by wiping the solid support over the solid sample, or over a solid surface containing the sample thereby smearing or accumulating sample present on a solid surface onto the porous support. Optionally the porous support can be first wetted with a liquid, e.g., water, and then used to wipe over the solid sample or over a solid surface containing the sample. Slurries can be brought into contact with the porous support by immersion or wiping.

Gas samples, e.g., air, that contain bacteria, spores, viruses or other nucleic acid components, as well as aerosols, also can be contacted with the porous support. For instance, a gas sample can be brought into contact with the porous support by means such as a blower, or by using vacuum suction to draw the gas sample towards and onto the porous support. The porous support can be wetted prior to being brought into contact with a gas sample.

Generally, nucleic acids that contact the porous support are not irreversibly bound to it. For example, nucleic acids can be stabilized by contact with the porous support and released from the porous support during elution.

Nucleic acid amplification inhibitors, e.g., a polymerase chain reaction (PCR), inhibitors, that contact the porous support are deactivated. In one embodiment of the invention, the porous support also retains solid contaminants. Preferably, the porous support also is capable of lysing or killing cells, spores, bacteria and other microorganisms, of inactivating RNases or DNases, or of lysing cells or spores to release nucleic acid. The porous support also can bind one ore more chemical compound, e.g., salts, used in preparing the nucleic acid component for amplification.

Generally, the porous support is water permeable. The porous support can be rigid or flexible and can be in the form of a pad, mat, disk, plug, thin layer, or can be in another suitable form. The porous support can be fabricated from silk, paper, cotton cloth, or other woven or non-woven materials, such as, for instance, natural or synthetic polymers, e.g., polyesters, polypropylene and others.

Generally, the porous support includes one or more agents that deactivate(s) a nucleic acid amplification inhibitor, e.g., a PCR inhibitor. The agent can change the secondary, tertiary or quaternary structure of biomolecule. The agent can induce precipitation, irreversible binding to the porous support or can denature nucleic acid amplification inhibitors. Deactivated components of the inhibitor are retained by the porous support or are soluble fragments that do not interfere with nucleic acid amplification procedures.

The agent also can disrupt cell membranes and cellular proteins to allow access to nucleic acid material present on or in the target cells.

To form the porous support, the agent can be impregnated into a suitable substrate or it can be otherwise incorporated or held by it. Substrates that are coated or chemically treated with the agent also can be employed. Methods for impregnating, chemically treating or coating substrates are known in the art.

In a preferred embodiment, the agent is a chaotropic salt. Examples of chaotropic salts include, but are not limited to, guanidine salts, e.g., guannidine isothiocyanate, guannidine thiocyanate, guannidine hydrochloride, sodium iodide, sodium perchlorate, potassium iodide, sodium (iso)thiocyanate, urea, or any combinations thereof.

Suitable porous supports are described in U.S. Pat. No. 5,496,562, issued to Burgoyne, on Mar. 5, 1996; U.S. Pat. No. 5,756,126, issued to Burgoyne on May 26, 1998; U.S. Pat. No. 5,807,527, issued to Burgoyne on Sep. 15, 1998; U.S. Pat. No. 5,972,386, issued to Burgoyne on Oct. 26, 1999; U.S. Pat. No. 5,976,572, issued to Burgoyne on Nov. 2, 1999; U.S. Pat. No. 5,985,327, issued to Burgoyne on Nov. 16, 1999; U.S. Pat. No. 5,939,259, issued to Harvey, et al., on Aug. 17, 1999; and U.S. Pat. No. 6,168,922, issued to Harvey, et al., on Jan. 2, 2001. The entire teachings of the above-referenced patents are incorporated herein by reference.

One specific example of a suitable porous support is paper available under the trade name of IsoCode®, which can be obtained from Schleicher and Schuell, Inc., Keene, N.H.

In one embodiment, the porous support is a chemically impregnated paper (e.g., IsoCode™, manufactured by Schleicher and Schuell, Inc. of Keene N.H., or improvements thereon) that binds PCR inhibitors, stabilizes nucleic acids, and subsequently releases the nucleic acid during an elution step.

The method of the invention includes the step of directing a fluid through the porous support. Preferably, the fluid is water and can include buffer compounds. Examples of buffer compounds include, but are not limited to TE (tris-EDTA), TAE (tris-acetic acid EDTA), TBE (tris-boric acid-EDTA), and deionized water. (Where EDTA is ethylene diamine tetraacetic acid.) Other fluids, such as, alcohols, also can be employed.

Directing generally is by active means that result in flow-through conditions of the fluid through at least a portion of the porous support. The fluid can be directed through the porous support, or portion thereof, by applying a force upon the fluid, for example by pressing a piston, lid, plunger, flexible membrane or other mechanical means upon the fluid. In a closed chamber, fluid can be directed through the porous support by compressing gas, e.g., air, above the fluid, for example by pressing a plunger or a flexible membrane. A pressure gradient also can be employed, e.g., by using a pump, vacuum or compression means to draw fluid through the porous support. The resulting flow-through of the fluid, together with a nucleic acid component, through the porous support, can be in any direction with respect to the porous support. In a preferred embodiment, fluid is directed from the face to which the sample is applied, through the porous support, to the opposite face.

Upon directing the fluid through the porous support, or through a portion thereof, the nucleic acid component in the sample is directed through at least a portion of the porous support. Nucleic acid amplification inhibitors and other contaminants described above are inactivated by and/or retained onto the porous support, while the nucleic acid component is separated from the support, generally with the eluted fluid. The nucleic acid component of the sample is thus prepared for amplification.

Optionally, compounds that are not present in the raw sample, but are introduced or generated during the preparation of the nucleic acid component for amplification, also can be removed. An example of such a compound includes a salt. For instance, salts can be removed by treating the fraction eluted from the porous support by a membrane designed for salt removal. Such desalting membranes are known in the art. Suitable examples include, but are not limited to, Sephadex beads, Sepharose beads, or ion-exchange membranes.

Proteins also can be removed. For example, proteins can be removed by using sepharose beads, cellulose beads or membranes.

Additional steps optionally can be conducted to enhance the separation of the nucleic acid component from the porous support, in particular with samples that contain low (trace) levels of nucleic acid(s).

One method for enhancing recovery of the nucleic acid component from the porous support is by applying heat. Heating can be in an oven, by immersion in an external hot bath, by heating coils, by blowing a hot gas or by other suitable means. The sample can be heated to a temperature in a range of between about 60° Centigrade (C) and about 95° C. In many cases, heating is at about 95° C. for about 30 minutes.

In another embodiment of the invention, recovery of the nucleic acid component from the porous support is enhanced by applying an electric field (electroelution) across the porous support containing the nucleic acid component of the sample. DNA, for example, has a net negative charge when in solution. In the presence of liquid with conductive ions and an electric field produced by two oppositely charged electrodes, wherein the negative electrode is applied to the porous support containing the nucleic acid component of the sample, DNA, for example, can be eluted from the porous support and caused to migrate to the positive electrode.

Preferably, the electrodes are coated to prevent irreversible adhesion of nucleic acids onto the electrodes. The electric field preferably is applied while the sample is in contact with the porous support. The electric field can be supplied by a direct current (DC) power supply. Generally, the voltage differential employed is in a range from about 0.5 volts (V) to about 20 V, generally for less than about 10 minutes, preferably for about 5 minutes. Current flow generally is less than about 1 nano ampere (nA). After the nucleic acids have been collected from the porous support, the voltage polarity may be reversed for a short period of time, preferably less than 5 seconds, to detach nucleic acids collected onto the positive electrode and resuspend them into the eluate.

The invention also is related to an apparatus suitable for preparing a nucleic acid component of a sample for amplification. The apparatus includes a porous support that deactivates a nucleic acid amplification inhibitor component of a sample contacting the porous support and a housing. The housing has an opening and defines an interior that is in fluid communication with the porous support, whereby at least a portion of a fluid directed through the opening is directed through at least a portion of the porous support and separates at least a portion of a nucleic acid component of a sample contacting the porous support from the support, thereby preparing the nucleic acid component for amplification.

For example, the porous support includes an agent that deactivates the nucleic acid inhibitor component of the sample, such as, for instance a chaotropic salt. Preferably the agent also kills cell or spores, deactivates DNases or RNases or lyses cells or spores to release nucleic acid.

One embodiment of the apparatus of the invention includes assembly 10, shown in FIG. 1. Assembly 10 includes housing 12 and container 14.

Assembly 10 is constructed in any suitable size. In a preferred embodiment of the invention, assembly 10 is sufficiently small to be portable, such as hand-held, and is suited for field applications. For instance, the largest dimension of assembly 10 can range from about 3 to about 13 centimeters. In one embodiment, assembly 10 is suitable for handling 50 microliter samples. Larger assembly 10 also can be constructed. In another embodiment, assembly 10 is constructed to be compatible with a commercially available PCR machine.

Assembly 10 is fabricated from any suitable material, preferably, a material that does not react with the substances with which it comes in contact. In a preferred embodiment, assembly 10 is fabricated, in whole or in part, from a plastic material, such as, for example, polycarbonate, nylon, polydialkylsiloxanes, polyethylene or polypropylene terephthalates, polytetrafluoroethylene and others. Assembly 10 also can be fabricated, in whole or in part, from glass or a metal such as, steel, aluminum and other materials. Combinations of materials also are suitable for fabricating assembly 10. Assembly 10 can be disposable after a single use.

Housing 12, includes tube 16 which defines interior region 18. Tube 16 can be cylindrical but can have another suitable shape. Tube 16 has ends 20 and 22. End 20 is open. End 22 is provided with means for receiving cap 24. Means for receiving cap 24 are, for instance, threaded groves 26 that match threaded grooves 28 on cap 24.

Other means for sealing end 22 also can be employed. For example, in an embodiment not shown in FIG. 1, end 22 is sealed by a press-fitted cap. In still another embodiment, also not shown in FIG. 1, the housing is constructed in an integrated fashion, with one sealed end. For instance, the tube can terminate in a narrow, elongated sealed ending that can be detached or broken, as known in the medical and pharmaceutical arts.

In a preferred embodiment, cap 24 is provided with dropper 30. In FIG. 1, dropper 30 is a medicine dropper and includes bulb 32 that can be squeezed and released to collect liquid from interior region 18 of tube 16. Other dropper designs also can be employed as known in the art. Access to interior region 18 of tube 16 also can be provided by employing a material that can be pierced by a syringe needle. For instance, means for sealing end 22 can be fabricated to include plastic film or a thin rubber insert, as known in the art, to allow access to interior region 18 via a hypodermic needle.

The size and wall thickness of tube 16 can vary depending on the sample being processes. Generally, the length tube 16 can be as small as about 1 centimeter and as large as about 12 centimeters with a diameter ranging from about 0.5 centimeters to about 3 centimeters.

Tube 16 includes porous support 34 at end 20. Porous support 34 deactivates a nucleic acid amplification inhibitor, as described above. In a specific embodiment of the apparatus, porous support 34 is a disk cut from IsoCode® paper.

Porous support 34 has interior face 36 and outer face 38.

Porous support is held at end 20 of tube 16 by retaining means 40 and positioning means 42. In one embodiment, retaining means 40 is an O-ring fitted at end 20 of tube 16. Edge clamps and other suitable means also can be employed to fabricate retaining means 40.

Positioning means 42 can be a lip in the interior wall of tube 16, a cross bar connected to the interior walls of tube 16 or other means. Positioning means 42 are located near end 20 of tube 16 at a distance suitable to accommodate the thickness of porous support 34 and any other inserts, further discussed below.

Optionally, mesh 44 is positioned at outer face 38 of porous support 34. Mesh 44 can be, for example, woven from strands of nylon, polypropylene, fluorocarbon, polyester, stainless steel or other metal. In a specific embodiment of the apparatus, mesh 44 is made of nylon and is 40 µm. Mesh 44 can retain solid impurities away from porous support 34 and can add rigidity and abrasion resistance to a thin, flexible porous support, such as, for instance, chemically treated cotton cloth or paper.

Optional desalting membrane 46 is positioned at interior face 36 of porous support 34. Desalting membrane 46 is fabricated from a material that retains ionic salt components, including, but not limited to, guanidine thiocyanate, magnesium ions, iron ions and others, as known in the art. Examples of suitable desalting membranes include, but are not limited to Sephadex/glass fiber composites, cation exchange membranes, and anion exchange membranes. More than one desalting membrane can be stacked in tube 16, onto interior face 36 of porous support 34.

Optional compression barrier 48 can be inserted between positioning means 42 and, either optional desalting membrane 46, or interior face 36 of porous support 34. Compression barrier 48 preferably is constructed from a plastic, incompressible material such as Teflon®, rubber, polypropylene, polyethylene, and others. Compression barrier 48 has channels 50. Compression barrier provides support for inserts at opening 20 and improves uniformity of the eluate volume removed from the porous substrate during flow through.

Figure 2:
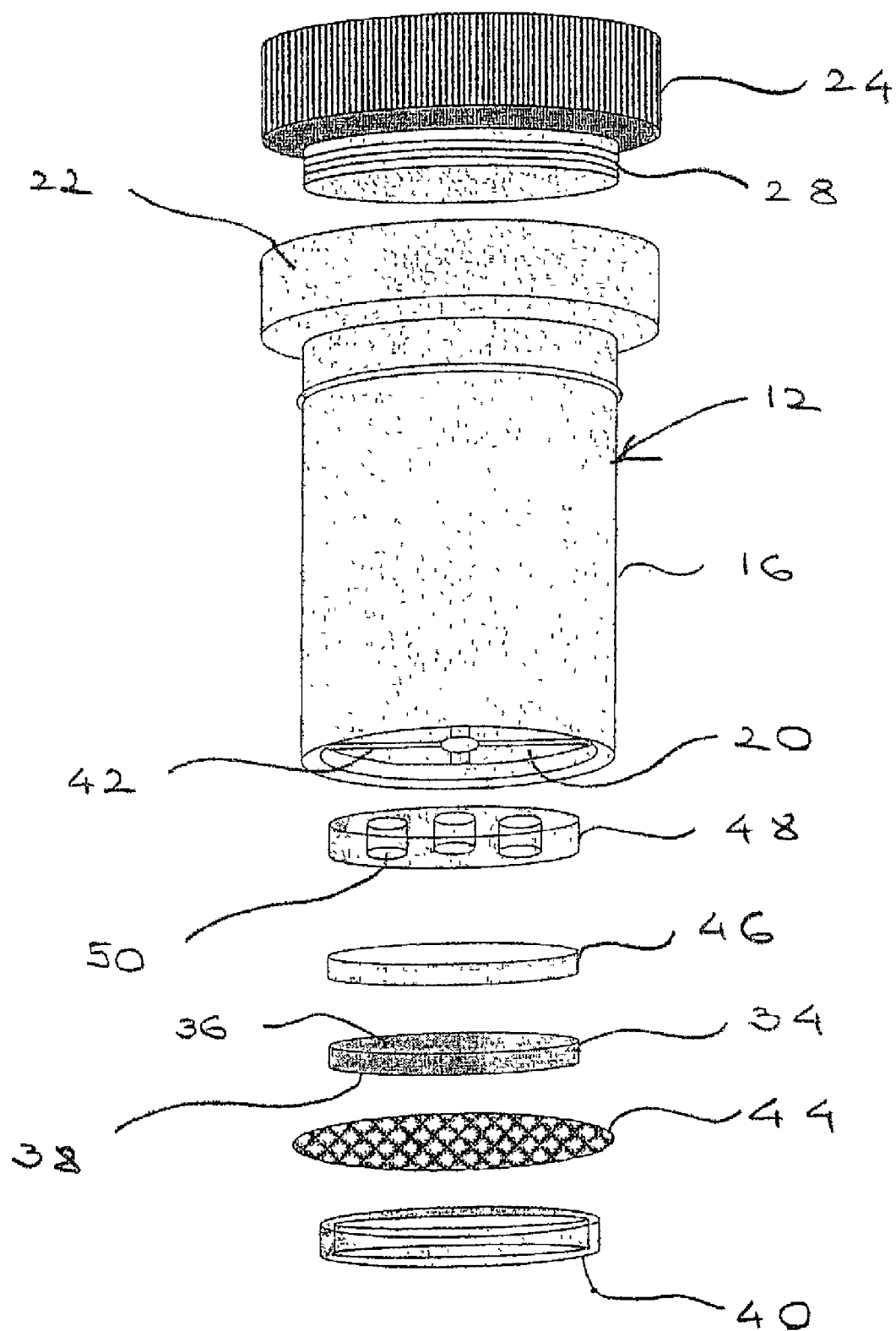
FIG. 2 is an exploded perspective view of a housing cap and porous support and other elements of one embodiment of the apparatus of the invention.

A side view of cap 24, tube 16, positioning means 42, compression barrier 48, desalting membrane 46, porous support 34, mesh 44 and retaining means 40 is shown in FIG. 2.

Container 14 (shown in FIG. 1) generally has a shape that conforms with the exterior surface of housing 12, such that when housing 12 is inserted into container 14, liquid present in container 14 is caused to flow through the porous support 34 and any other inserts.

Optionally, assembly 10 can be provided with means for applying an electric field, to enhance release of charged nucleic acids, held by porous support 34. In one embodiment, electrodes are positioned, respectively, at the end of bulb 32 and above mesh 44. In another embodiment, electrodes are embedded in positioning means 42 and mesh 44. Mesh 44 and positioning means 42 can be fabricated from of a conductive material, such as a metal, coated with a biologically-inert substance nonadherent to DNA. Contact to positioning means 42 can be made by means of a conductive material path embedded in the wall of tube 16 and leading from positioning means 42 to the outer walls of assembly 10. Generally, the electrode having a charge opposite that of a nucleic acid is positioned to attract the nucleic acid away from porous support 34 and towards interior region 18 of tube 16. Both electrodes can be connected to a DC power supply, as known in the art.

During operation, a raw sample, e.g., a solid, slurry, liquid or gas sample is contacted with porous support 34, optionally through mesh 44. The sample remains in contact with the porous support for a short interval, e.g., a few minutes. Housing 12 is then inserted into container 14 which preferably encloses a suitable amount (e.g., about 25 to about 100 microliters (µl) in the case of a small, portable assembly 10) of the fluid reagent employed, e.g., water or water and buffer compounds, such that end 20 of tube 16 faces bottom 52 of container 14. Housing 12 is pressed towards bottom 52 of container 14, thereby forcing the fluid reagent through porous support 34 and optionally through desalting membrane 46, and any other inserts, to interior region 18 of tube 16. The nucleic acid component is eluted together with the flow-through fluid, to interior region 18 of tube 16, and is ready for amplification. It can be removed from housing 12 by dropper 30 or by other means, e.g. syringe. The nucleic acid component also can be stored or archived in the eluted fluid in assembly 10.

In one embodiment of the invention, a nucleic acid component prepared as described above is further processed, e.g., by PCR procedures, as known in the art. For instance multiple samples can be collected and processed using multiple assemblies 10 each as described above. A manual press can be employed to process, for example, six assemblies at a time. An automatic press, e.g. COTS Whatman Mini-Uniprep Processor model #PR0000040, can be employed to process, for instance a batch of thirty assemblies. Signal analysis and procedures by which nucleic acids and organism from which they originate are identified also are known in the art.

Another embodiment of the apparatus of the invention includes cartridge 60 which includes a plurality of wells. Cartridge 60 and its operation are further described with respect to FIGS. 3, 4 and 5.

Figure 3:
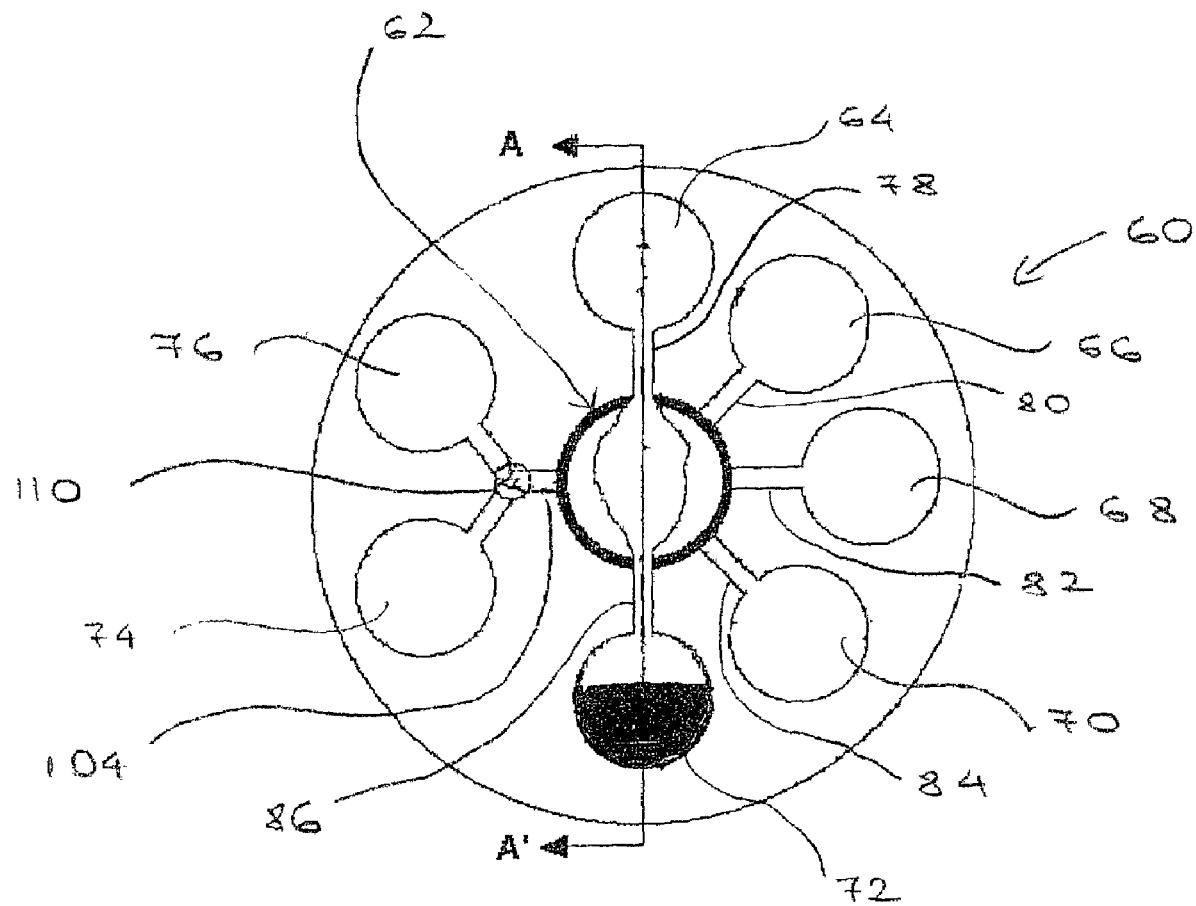
FIG. 3 is horizontal cross sectional view of an embodiment of the apparatus of the invention.
Figure 4:
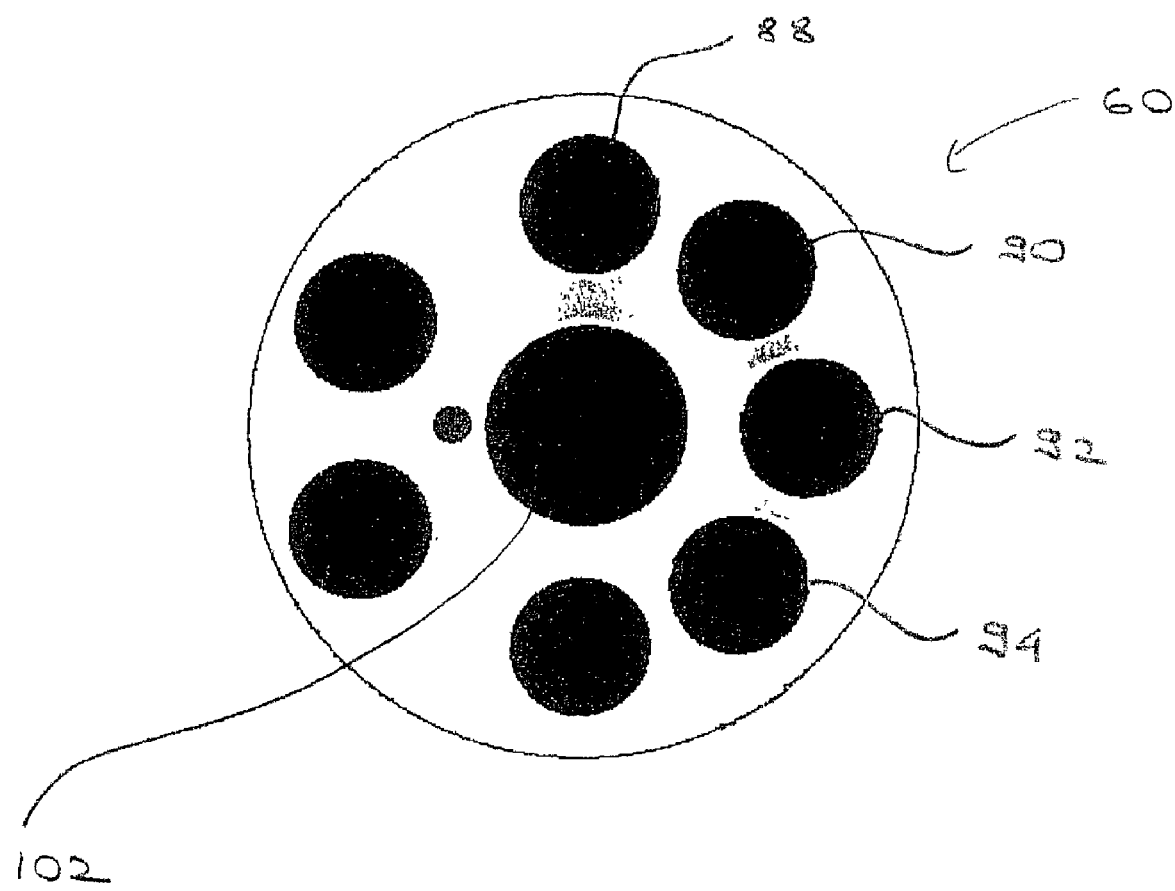
FIG. 4 is a top view of an embodiment of the apparatus of the invention.
Figure 5:
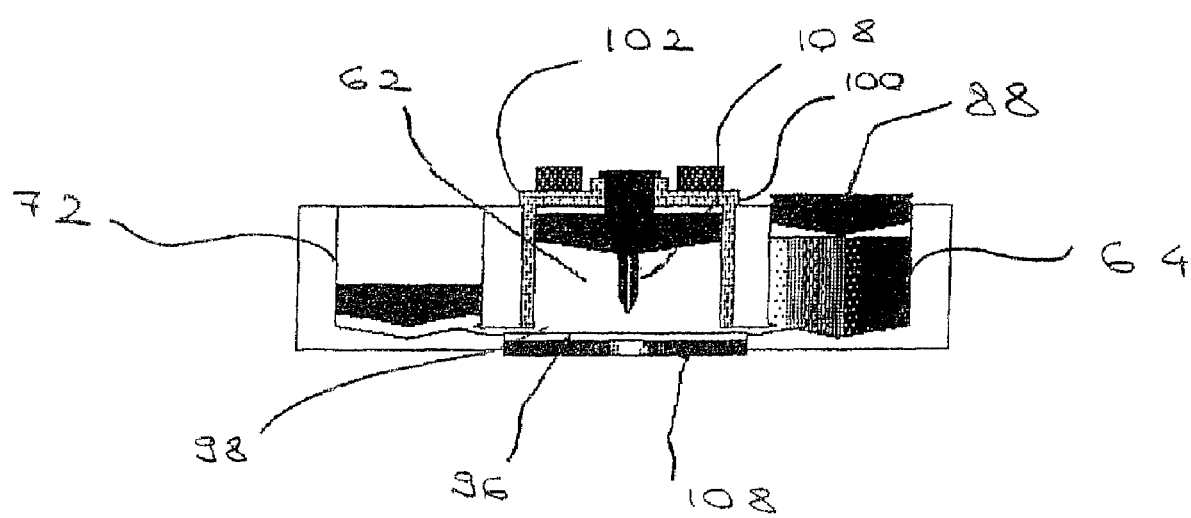
FIG. 5 is a cross sectional view along cutaway line AA$^1$ in FIG. 3.

Specifically, a horizontal cross sectional view of cartridge 60 is shown in FIG. 3, a top view, in FIG. 4 and a cross sectional view along cutaway line AA' of FIG. 3, in FIG. 5.

Cartridge 60 can be fabricated from a suitable material, preferably a plastic material, such as for example, polycarbonate, nylon, polydialkylsiloxanes, polyethylene or polypropylene terephthalates, polytetrafluoroethylene and others. Cartridge 60 also can be fabricated, in whole or in part, from glass or a metal such as steel, aluminum and other materials. Preferably, cartridge 60 is fabricated for a single use. Cartridge 60 has dimensions in the range of from about 5 centimeters to about 10 centimeters. Cartridge 60 includes a plurality of wells, specifically sample well 62 and chambers 64, 66, 68, 70, 72, 74 and 76. Generally, all the chambers are completely encapsulated in cartridge 60. In the embodiment shown in FIGS. 3 and 4, chambers 64, 66, 68, 70, 72, 74, 76 are arranged around sample well 62. Other arrangements of the chambers with respect to sample well 62 also can be employed.

Input chambers 64, 66, 68, 70 store reagents that are delivered to sample well 62. For example, chamber 64 stores wash water, chamber 66, elution water, chamber 68, buffer and chamber 70, reagent. Reagents and/or buffers can be stored in liquid form or can be stored in dry form and solubilized by adding water from additional input reservoirs (not shown in FIGS. 3, 4 or 5) immediately prior to use. Preferably all reagents or fluids necessary to prepare a nucleic acid component in the sample for amplification are preloaded in cartridge 60 during manufacturing.

Output chambers 72, 74, 76 include collection chambers 74 and 76 (for product and waste, respectively) and used wash water receptacle 72. Depending on a particular sample and protocol, not all chambers shown in FIGS. 3 and 4 need to be employed.

Conduits 78, 80, 82 and 84, extend, respectively, from input chambers 64, 66, 68 and 70, to sample well 62. Sample well 62 can be provided with ports that are alignable with conduits 78, 80, 82 and 84.

Cartridge 60 is provided with means for selective communication between an input chamber and sample well 62. For example, selective communication can be achieved using a rotatable wall with one or more openings that align openings in sample well 62 with conduits to the other reagent chambers. In a preferred embodiment, the rotatable wall has two openings that align so that wash water can be introduced in sample well 62 and can exit sample well 62, via conduit 86, to wash water receptacle 72. Receptacle 72 can enclose a superabsorbent or a gel-like material that prevent subsequent leakage or spillage of wash water.

Other suitable means for providing selective communication between a chamber and sample well 62 include, slots or pins that can be manipulated manually or automatically. Input chamber 64, 66, 68 and 70, for example, can be constructed so that a wall area at conduits 78, 80, 82 and 84, respectively, bursts under pressure or if punctured, thereby providing selective fluid communication between each chamber 64, 66, 68 or 70 and sample well 62. In another example, fluid stored in a chamber can be expelled into sample well 62 by pressurizing the roof of the chamber, which includes an elastic membrane. Pressurizing results in the breakage of a seal membrane on the wall of the sample well. The base of each input chamber is shaped to result in complete expulsion of the fluid, as the elastic membrane is pressed down. Plungers 88, 90, 92 and 94 (shown in FIG. 4) also can be depressed to expel a fluid from any of chambers 64, 66, 68 or 70, as shown in FIG. 5 for chamber 64.

Sample well 62 can have any suitable dimensions. In one example, sample well 62 is sized to receive a fluid sample of up to about 5 ml.

In the interior of sample well 62, wall surfaces can be partially coated with a hydrophobic coating to enhance confining the sample and water-based reagents to the lower section of the well. Similar hydrophobic coatings can be provided to any of the other chambers in cartridge 60.

As seen in FIG. 5, sample well 62 includes porous support 96 that deactivates a nucleic acid amplification inhibitor, e.g., an insert of IsoCode® paper. Porous support 96 is placed at lower end 98 of sample well 62.

Upper end 100 of sample well 62 is covered or sealed. In the embodiment shown in FIG. 4, sample well 62 is covered by lid 102 that includes an embedded gas-permeable membrane. The lid can be sealed, for instance, by a snap closure and an O-ring gasket. The gas-permeable membrane allows venting of vapors, e.g., water vapors generated during a heating step to dry a sample deposited on the porous support. Other means for sealing sample well 62 or for allowing venting of vapors also can be employed, as known in the art. For instance, sample well can be sealed with a cap provided with a relief valve.

Fluid communication also is established between sample well 62 and collection chambers 74 and 76, as seen in FIG. 3.

In one embodiment, collection chambers 74 and 76 are under vacuum. Pressure being applied onto fluid in sample well 62, for example by plunger means, or by applying force onto the gas-permeable membrane in lid 62, can cause rupture of a membrane closure at conduit 104. A membrane seal between sample well 62 and conduit 104 also can be ruptured by a pin puncture, effected manually or automatically. Contents in sample well 62 can thereby be emptied in collection chambers 74 or 76, as further described below.

During operation, a raw sample is introduced in sample well 62 and into contact with porous support 96 for instance through the hinged lid described above. No further access to cartridge 60 is necessary.

Selective fluid communication between sample well 62 and input chambers 64, 66, 68 and 70 is established in an order established by the protocol being used. Various reagents and fluid(s) are directed to sample well 62 and to porous support 96 via plungers or other suitable means, as discussed above.

The raw sample can be subjected to an electric field by electroelution electrodes 106 and 108. The electrodes are connected to a power supply, not shown in FIG. 5, of up to about 20V. Preferably, the electrode surfaces are treated to prevent attachment of nucleic acids. Electrode 108, at lid 102 can be flat or can have a pointed tip to provide electric field enhancement, as known in the art.

Heating also can be employed, alternatively or in combination with applying an electric field. Heating can be by external heating means or can be built into the cartridge design. In one example, thermoelectric heating can be employed. For many samples, heating, in the absence of an electric field, is for about 30 minutes at about 95° C.

Elution can include a concentration step in order to reduce the volume of the nucleic acid component. A binding matrix 110 is employed to retain nucleic acid while initial wash fluid is directed to collection chamber 76 (waste). Access to chamber 76 is then closed and nucleic acid is released from binding matrix 110 by introducing elution fluid, e.g., water, to elute bound nucleic acid from binding matrix 110 to collection chamber 74 (product).

Suitable materials that can be employed to form binding matrix 110 include, but are not limited to, silica or glass.

Furthermore, collection chambers 74 and 76 can be sealed by means of heat-sealable membranes, heated with pins, not shown in FIGS. 3, 4 or 5. Thus product nucleic acid components can be stored in suspension in cartridge 60.

The sample also can be removed with a hypodermic needle that punctures cartridge 60, at a product withdrawal port, not shown in FIGS. 3, 4 or 5.

Sample well 62 and chambers 64, 66, 68, 70, 72, 74 and 76 essentially as described above can be integrated with a nucleic acid hybridization, and optionally, amplification chambers.

Figure 6:
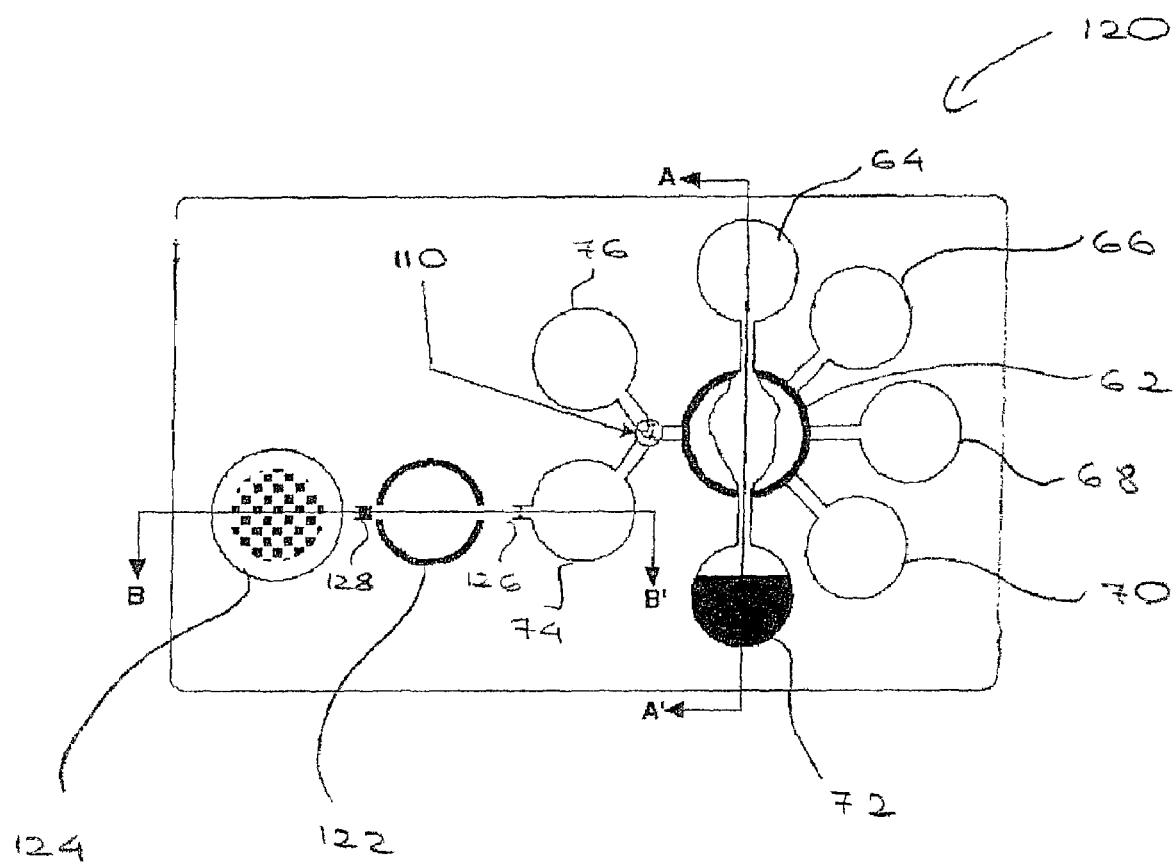
FIG. 6 is horizontal cross sectional view of an embodiment of the apparatus of the invention.
Figure 7:
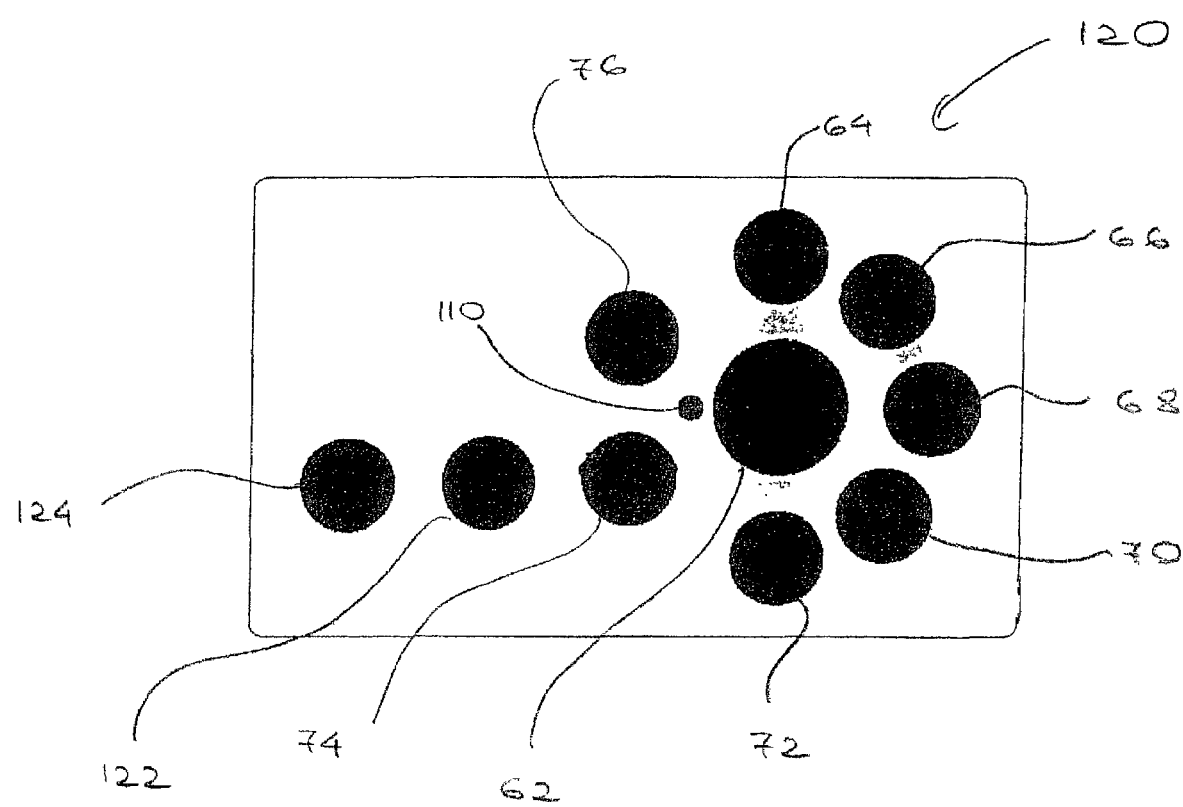
FIG. 7 is a top view of an embodiment of the apparatus of the invention.
Figure 8:
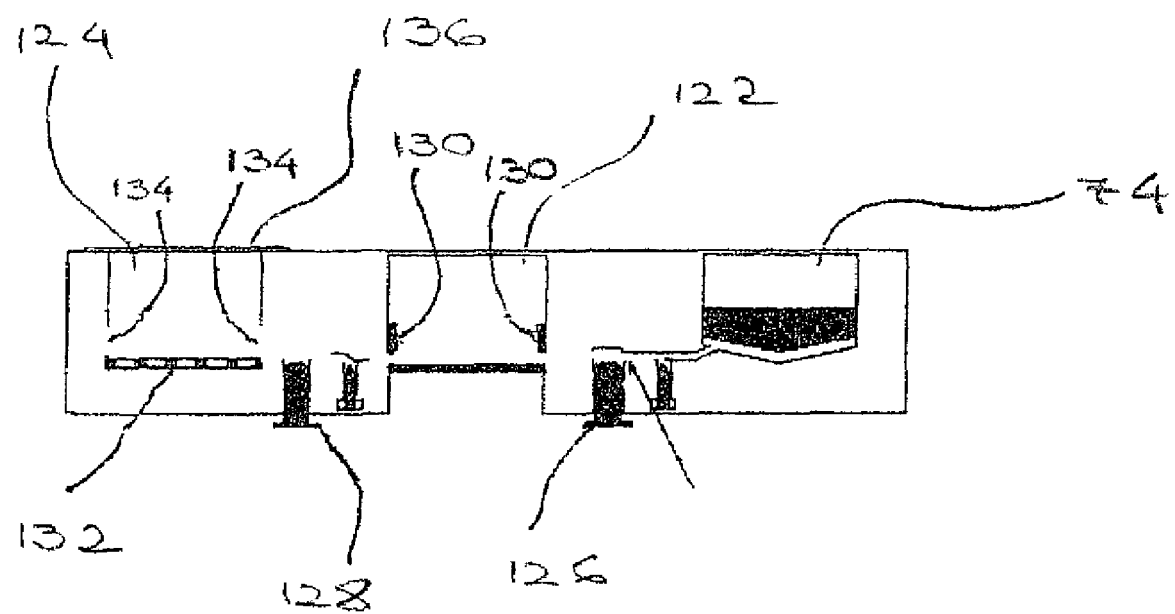
FIG. 8 is a cross-sectional view along cutaway line BB¹ in FIG. 6.
Figure 9:
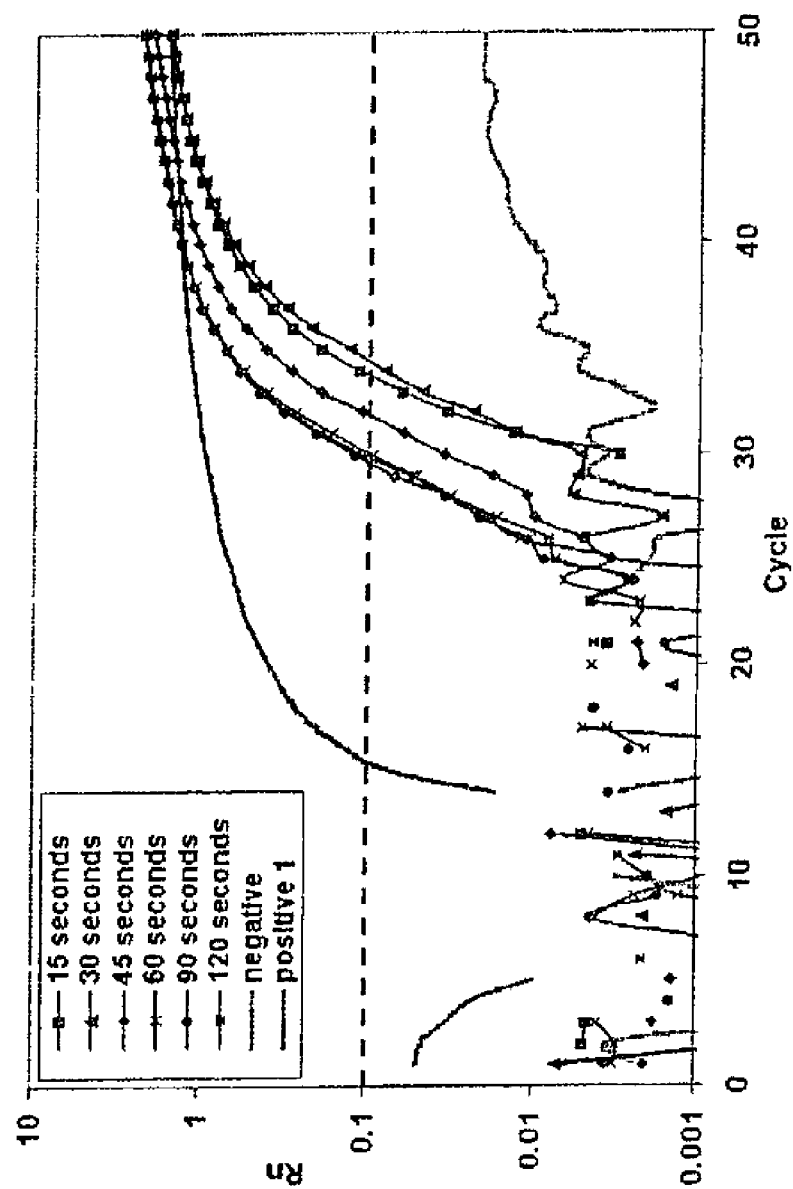
FIG. 9 presents a series of plots showing relative signal fluorescence level vs. amplification cycle number from air samples contacting a porous support according to the invention.
Figure 10:
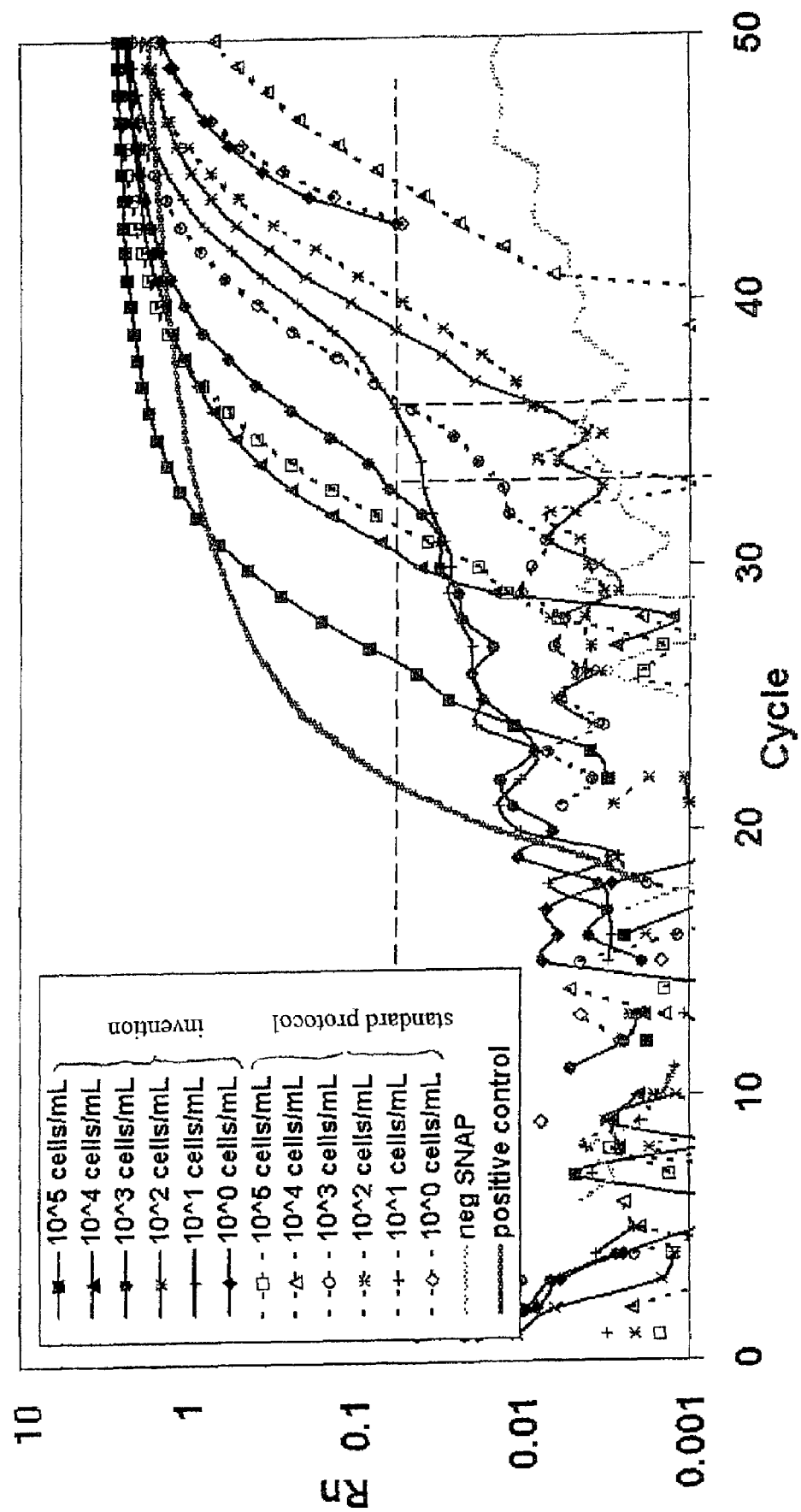
FIG. 10 presents a series of plots showing relative signal fluorescence level vs. amplification cycle number from various samples prepared by embodiments of the method and apparatus of the invention and by a comparative technique.
Figure 11:
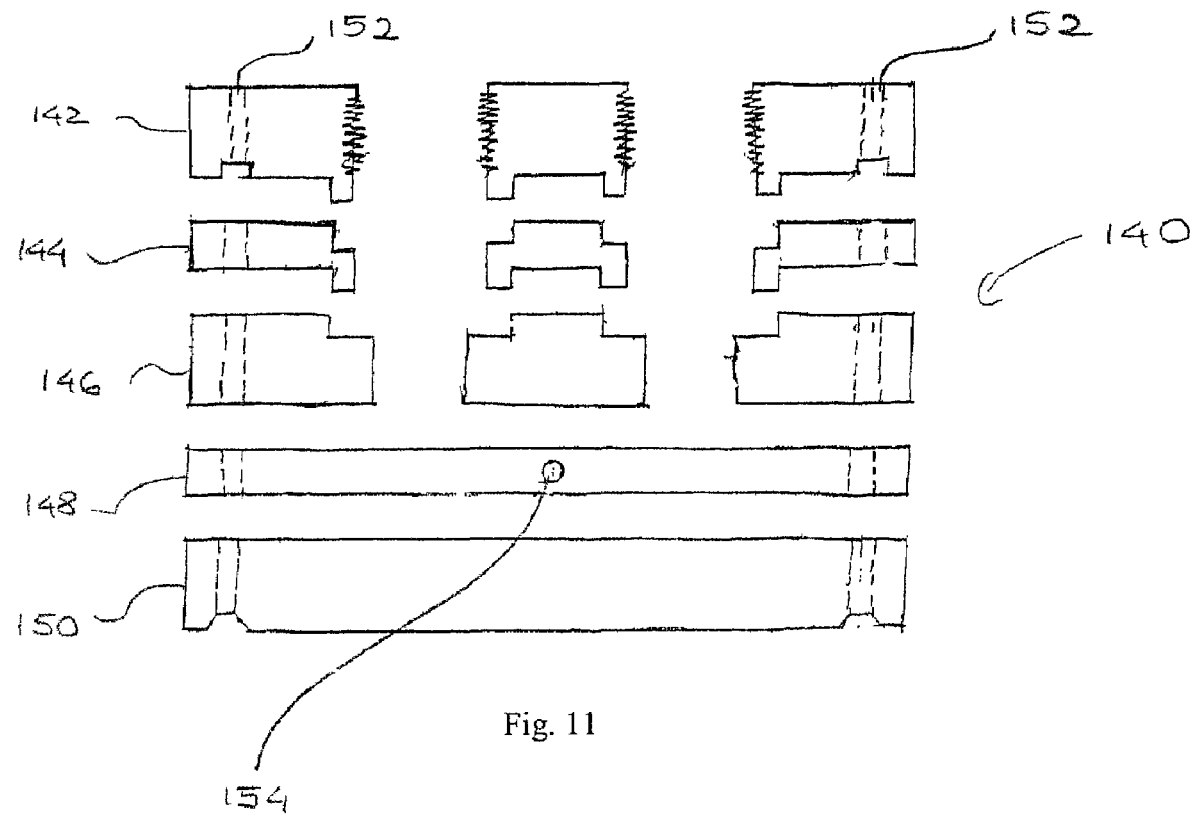
FIG. 11 is a cross-sectional view of an electroelution device for applying electric current to enhance removal of an amino acid from the porous support.
Figure 12:
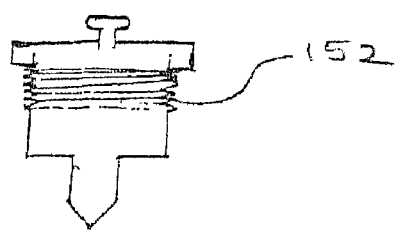
FIGS. 12 and 13, respectively, are cross-sectional and top views of an electrode employed in the device shown in FIG. 11.
Figure 13:
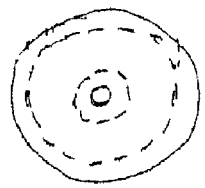
Figure 14:
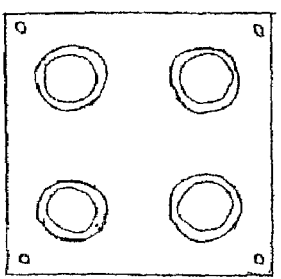
FIGS. 14–18 are top views of individual plates employed in the device shown in FIG. 11.
Figure 15:
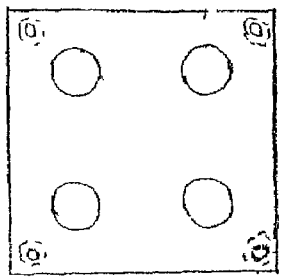
Figure 16:
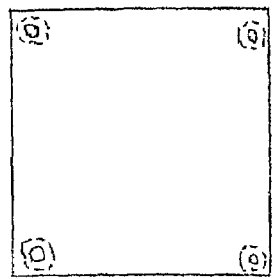
Figure 17:
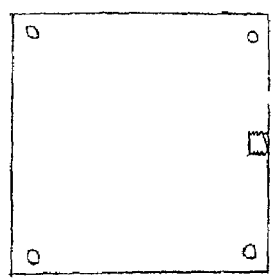
Figure 18:
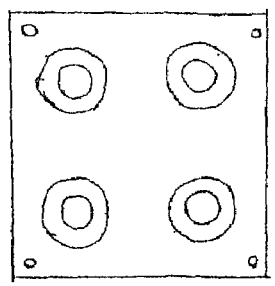

Integrated cartridge 120 is described with respect to FIGS. 6, 7 and 8.

In addition to the elements described above, integrated cartridge 120 includes amplification chamber 122 and hybridization chamber 124. Conduits for fluid communication are provided, respectively, for fluid communication between collection chamber 74, containing a nucleic acid component that is ready for amplification, to amplification chamber 122 and from amplification chamber 122 to hybridization chamber 124.

Nucleic acid amplification and hybridization procedures are known in the art.

Amplification chamber 122 receives the required primers and enzymes from a separate input reagent chamber (not shown), which can be pressure actuated as described above. Heat for the amplification reaction, if required, is supplied from an external source to the heater cavity, also not shown. Dry reagents 130 also can be provided. The chamber is prefabricated to be under vacuum, and accessed and sealed with heated pins 126 and 128 as described above. Hybridization chamber 124 contains array 132 of DNA/RNA printed on the base of the chamber. The interior walls of chamber 124 are coated with colorimetrically or fluorescently labeled oligonucleotide probes 134 which dissolve when hydrated and are used to detect hybridization. Alternatively, the probes and other reagents can be provided in the form of dried beads containing the reagents, which are rehydrated and dissolve when the fluid sample from collection chamber 74 is introduced into the hybridization chamber 124. The chamber has lid 136 fabricated from a transparent membrane, to allow observation of the array.

The invention is further illustrated by the following examples which are not intended to be limiting.

EXEMPLIFICATION

Example 1

A general commercial method for using IsoCode® paper includes the following steps:
Apply sample directly to IsoCode® paper;
Dry via desiccation or baking;
Rinse by vortexing in dH$_2$O;
Submerge rinsed IsoCode in dH$_2$O and heat at 95° C. for 30 minutes;
Pulse vortex to remove DNA from paper; and
DNA is ready for PCR amplification.

A detailed protocol for preparing a DNA component of a raw solid sample (preferred to as the matrix), that can be prepared into a slurry, for amplification by employing IsoCode® paper, in the absence of the invention, is shown as Comparative Protocol A.

Comparative Protocol A
1. Measure 50 mg of the matrix into aluminum weighing dish (or any hydrophobic, non-silica-based weighing container).
2. Place a triangle of IsoCode® paper into another clean weighing dish.
3. Add as much distilled water to the matrix as is needed to be able to remove 15 μL from the sample. This is usually 25–30 μL for sandy soils, 35–40 μL for finer-grained or clay-containing soils, and a variable amount for other matrices.
4. Mix the matrix and the water well with the pipette tip used to add the water to the sample, until a fairly uniform slurry is formed. Pipette up and down if possible, to increase sample mixing. Use filter tips to minimize pipette contamination.
5. With the same pipette tip, extract approximately 15 μL of liquid from the slurry; this may have some amount of suspended solids in it.
6. Apply the liquid to IsoCode®.
7. Bake IsoCode® piece for a minimum of 15 minutes (or until totally dry) at 60° C. under vacuum, or let dry for a minimum of 4 hours with desiccant in a sealed container at room temperature.
8. Remove dried IsoCode pieces from oven, and for each sample prepare a 1.5 -mL-tube with 500 μL of distilled water (wash tube) and a 0.5 -mL-tube with 50 μL of distilled water (eluate tube). The eluate tubes need to be labeled with sample numbers, the wash tubes do not.
9. Without touching the piece of IsoCode®, place it in the wash tube. Close the cap and vortex 2–3 times for 1 second each.
10. Uncap the tube, and using a clean pipette tip, remove the piece of IsoCode® and place into the eluate tube, and close the tube. Make sure that the IsoCode® is completely submerged and that there are no air bubbles in contact with it. Discard wash tube. Repeat with remaining samples, using a fresh pipette tip each time.
11. Using the thermocycler or heating block, heat all eluate tubes at 95° C. for 30 minutes. If the tubes cannot be postprocessed immediately after this step, cool them to 4° C. and hold.
12. When the tubes have cooled, remove them fro the thermocycler and remove each piece of IsoCode® from its tube, using a pipette tip to extract as much liquid as possible from the paper into the tube before discarding the paper.
13. The eluate is ready for PCR analysis.

Protocol B was developed to include the method of the invention for being conducted in an assembly such as assembly 10, described above and illustrated in FIG. 1.

Protocol B
1. Apply sample to porous support (IsoCode® paper), by dropping liquid sample on it or wiping surface to be sampled.
2. Wait 5 minutes.
3. Push water or buffer-containing water through porous support by inserting the housing of the assembly into the container which already encloses 100 microliters of the water or buffer-containing water.
4. Remove the eluate (water containing nucleic acid component of the sample) with a pipette tip after opening the housing of the assembly by removing the removable cap.

A comparison of the two protocols, Comparative Protocol A and Protocol B illustrate the reduced time and number of steps necessary to prepare a nucleic acid component for amplification when using the method of the invention and an embodiment of the apparatus of the invention. For example, both drying cycles have been eliminated. (In some of its embodiments, the method of the invention optionally can include a single heating step or can employ electroelution, to enhance removal of the nucleic acid components from the porous support.)

Materials and Methods for Examples 2, 3 and 4

PCR Amplification Procedures and Data Analysis

Data was obtained from a polymerase chain reaction (PCR) amplification procedure (hereafter referred to as TaqMan) performed on a series of DNA samples using the ABI PRISM® 7700 Sequence Detection System (part #7700-01-200/208, manufactured by Applied Biosystems, 850 Lincoln Centre Drive, Foster City, Calif., 94404).

The TaqMan system works by amplifying the DNA present in the sample with a "normal" PCR technique, while simultaneously monitoring the quantity of DNA being replicated in real time. This is accomplished as follows:

A normal PCR cycle starts. The DNA is denatured, and the probes for either end of the sequence to be replicated bind. At this point, a specialized probe also binds to the middle of the sequence. It is labeled with a fluorogenic "reporter" dye on one end, and a "quencher" on the other. When these two molecules are in close proximity (i.e. bound to the same strand of DNA) the fluorochrome is quenched by the quencher molecule and no light is given off.

Once the probes at either end of the sequence have bound, the DNA polymerase progresses along the DNA, making the single strand double stranded. When it reaches the fluorogenically labeled probe, its 5' nuclease activity cleaves the probe into separate bases as it progresses down the strand. This liberates the fluorophore, allowing it to move away from the quencher, and permitting it to fluoresce.

The TaqMan measures the fluorescence intensity inside the tube at each cycle and records it for analysis by the software. Each cycle doubles the number of DNA strands with the correct sequence, and the corresponding fluorescent signal being recorded by the TaqMan at the end of the cycle.

Data is shown in the form of a logarithmic-linear plot, with relative signal fluorescence level (Rn) on the y-axis and the amplification cycle number (Cycle) on the x-axis. A detection threshold is set by the user, and any signal exceeding the detection threshold level and following the exponential amplification curve shape shown in the plot is considered to be a "positive hit". The cycle number at which the detection threshold is exceeded is referred to as the cycle threshold for that particular sample. A lower cycle threshold indicates a larger starting quantity of DNA in the sample (all other factors in the sample being equal).

Description of Seeding Procedures Used

Vegetative bacterial cultures are prepared in bacterial growth medium, from frozen stocks of bacteria. Cultures are grown overnight, to late log phase growth stage, and typical cultures contain approximately $10^7$ cells/mL of growth medium. Dilutions of the stock culture used for seeding are prepared by volumetric dilution in a diluent of growth medium, or the liquid in which the sample is to be seeded. A typical dilution series consists of dilutions from 1:10 (bacterial culture:diluent) down to $1:10^6$, by factors of 10. Samples are mixed by vortexing.

Example 2

Dry spores were collected from air onto a porous support in an assembly such as assembly 10, described above and shown in FIG. 1.

A commercial mini vacuum cleaner, obtained from Microcenter, Cambridge Mass. was adapted to hold the assembly. The air stream was directed towards the porous support at one end of the assembly.

Once a sample was collected onto the porous support, nucleic acid component in the sample was prepared for amplification using Protocol B, steps 2 to 4, described in Example 1.

TaqMan amplification results for samples collected by air impaction for periods ranging from 15 seconds to 2 minutes are shown in FIG. 9. The results indicate that impaction times of as low as 15 seconds (translating to particle counts of thousands of particles per liter of air) were sufficient to detect and identify the target spore particles.

Example 3

An assembly such as described above with respect to FIG. 1 was employed to prepare nucleic acid components of several samples for amplification. Samples were prepared by seeding dust contaminated water with bacterial cell cultures at various dilutions. Samples were processed using comparative protocol B, and the standard protocol given by the manufacturers of IsoCode. TaqMan amplification results are shown in FIG. 10. Results indicate that reductions in cycle thresholds were obtained in all samples using the assembly described in FIG. 1, as compared to identical samples processed using the standard protocol.

Example 4

Protocol C was developed to demonstrate the advantages of applying an electric field in conjunction with a porous support capable of deactivating a nucleic acid amplification compound in a sample. Protocol C was conducted with an electroelution device.

A cross-sectional side view of such a device, electroelution jig 140 is shown in FIG. 11. Electroelution jig 140 includes plates 142, 144, 146, 148 and 150 which can be assembled stacked upon each other by using screws and nuts through channels 152. Plates 142, 144, 146, and 150 are fabricated from a material such as Plexiglas, polycarbonate, or other inert material that does not adhere DNA. Plate 14 is fabricated from a conductive material such as a metal.

Plate 142 is threaded to receive 4 collection electrodes 152. A cross-sectional view of one electrode 152 is shown in FIG. 12 and a top view of FIG. 13.

Top views of each of plates 142, 144, 146, 148 and 15 are shown respectively in FIGS. 14, 15, 16, 17, 18.

Plate 148 and electrode 152 are made from a conductive material such as a metal.

Voltage can be applied to plate 148 and electrode 152 (e.g., via screw 154) and screws 152 from an external source, e.g., DC battery, not shown in FIG. 11. Preferably, plate 148 is the negative electrode and electrode 152 are the positive electrode. In jig 140 a porous support, e.g., IsoCode® paper, can be placed in the wells created by plate 146, or can be clamped between plates 146 and 148 (the negative electrode). Size-exclusion filters (e.g. 100 Daltons (Da) size) of a size to exclude all particles except the nucleic acid component of the sample, can be clamped between plates 144 and 146 and between plates 142 and 144 to permit the eluted DNA to pass to electrode 152 (the positive electrode).

Protocol C

1. Prepare IsoCode® samples as per steps 1–7 in the basic protocol (as described in Comparative protocol A).
2. Assemble lower portion (plates 150, 148, 146) of electroelution jig 140. DNA to pass to electrode 152 (the positive electrode).
3. Place IsoCode® paper into sample well electroelution jig 140.
4. Add filtered distilled water to top of well.
5. Add 100 Da cellulose acetate membrane.
6. Assemble upper potion of jig 140 (plates 144, 142) to lower portion. Add filtered distilled water to well.
7. Insert upper electrode 152 into jig 140.
8. Apply voltage to electrodes 148 (negative electrode) and 152 (positive electrode) for 5 minutes.
9. Remove voltage source. (Alternatively, the upper electrode may be reverse-biased momentarily to drive off any nucleic acid components that may be adhered to electrode 152.
10. Remove electrodes 152. Remove eluate containing nucleic acids from well and place in 0.5 -mL tube.
11. Discard paper and membrane(s).
12. The eluate is ready for PCR analysis.

The jig illustrated in FIGS. 11–18 was tested using electroelution conditions, as follows: voltage=(0.5, 1, 2, 5, 10, 20V), elution time=(1, 5, 10 minutes), buffer=water.

With respect to comparative protocol A, protocol C using electroelution could be completed in 5 minutes rather than in excess of 30 minutes, as a result of the elimination of the 30 minute heat step. Preliminary results indicated that the wash step (step 9) in comparative protocol A may not be required when employing protocol C.

Figure 19:
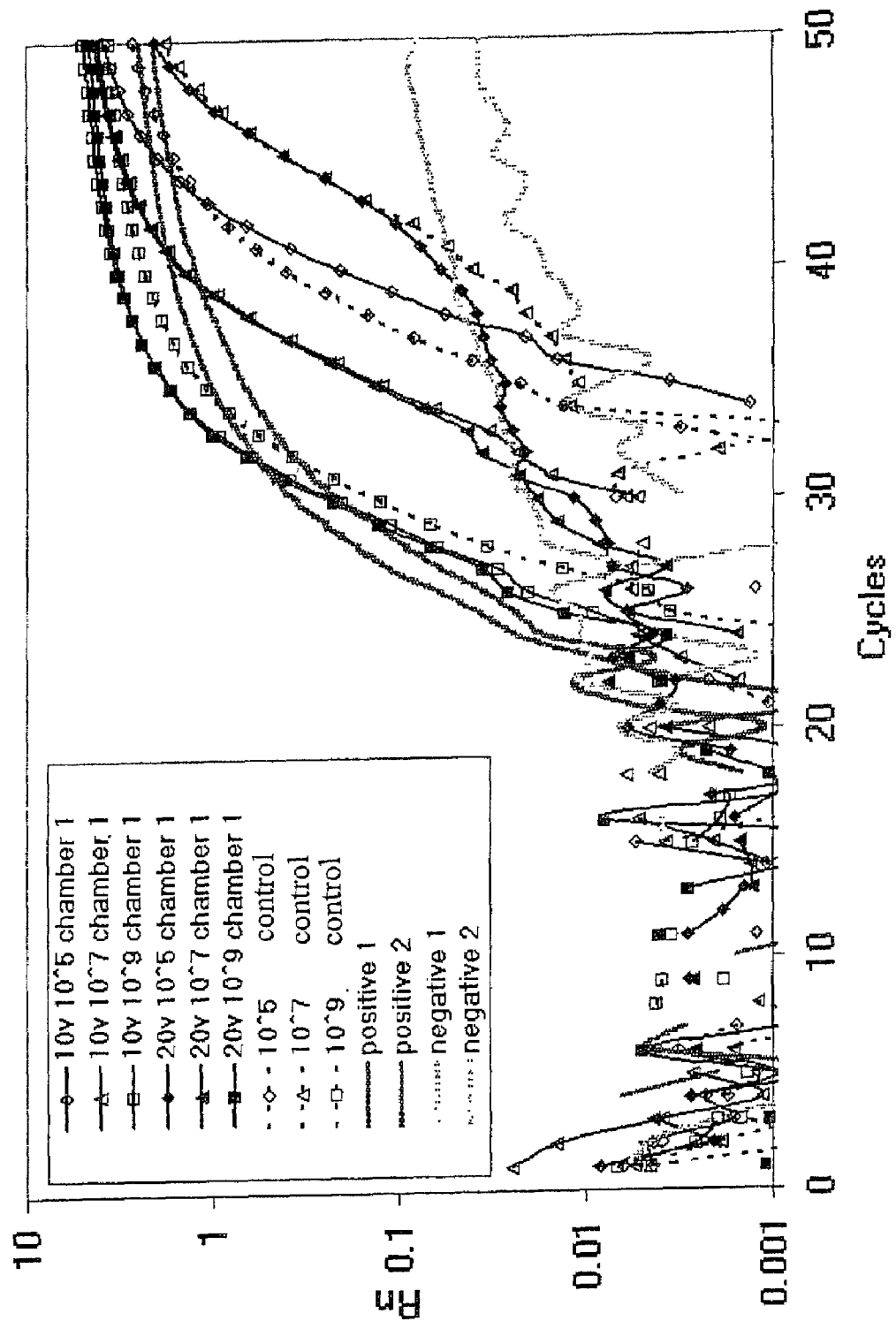
FIG. 19 is a series of plots showing detection improvements in analyzing samples prepared in a device such as described in FIGS. 11–18.

FIG. 19 shows results of an experiment conducted using an electroelution jig such as described above and shown in FIGS. 11–18, for the elution step, and an ABI PRISM 7700 Sequence Detection System for PCR amplication. Samples were vegetative bacterial cells seeded into a sandy soil. For the $10^9$ cell/gram level, there was an improvement of 7 cycles in detection cycle threshold. For the $10^5$ cell/gram seeded level, no improvement was seen in this experiment but that is sometimes typical due to statistical variation from sample to sample at the lower seeding levels. Results are shown in FIG. 19.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preparing a nucleic acid component of a sample for amplification, comprising the steps of:
    a) contacting the sample with a porous support that deactivates a nucleic acid amplification inhibitor component of the sample, wherein the porous support includes a deactivating agent that deactivates the nucleic acid amplification inhibitor component of the sample; and
    b) directing a fluid through the porous support, whereby the nucleic acid component of the sample is directed through at least a portion of the porous support and is separated from said porous support and from said nucleic acid amplification inhibitor component at said porous support, whereby deactivated components of the nucleic acid amplification inhibitor component are retained by the porous support or are soluble fragments that do not interfere with nucleic acid amplification procedures, thereby preparing the nucleic acid component for amplification.

2. The method of claim 1, wherein the agent is a chaotropic salt.

3. The method of claim 2, wherein the chaotropic salt is guanidine thiocyanate.

4. The method of claim 1, wherein the agent further kills or lyses cells or spores in the sample.

5. The method of claim 1, wherein the agent further deactivates DNases or RNases in the sample.

6. The method of claim 1, further including the step of applying an electric field to the sample while the sample is contacting said porous support, whereby said electric field facilitates separation of the nucleic acid component from the support and from the deactivated nucleic acid amplification inhibitor component.

7. The method of claim 1, further including the step of contacting a buffer solution with the porous support while the porous support is contacting the sample.

8. The method of claim 1, further including the step of heating the sample while the sample is contacting the porous support, whereby said heating facilitates separation of the nucleic acid component from the porous support and from the deactivated nucleic acid amplification inhibitor components.

9. The method of claim 8, wherein the sample is heated to a temperature in a range of between about 60° C. and about 95°C.

10. The method of claim 1, further including the step of stabilizing the nucleic acid component of the sample.

11. The method of claim 10, wherein the nucleic acid component of the sample is stabilized by contacting the sample with a chaotropic salt.

12. The method of claim 1, further including the step of separating the nucleic acid component of the sample from the deactivating agent.

13. The method of claim 12, wherein the nucleic acid component of the sample is separated from the deactivating agent by directing the fluid and the nucleic acid component through a membrane that retains the deactivating agent.

14. The method of claim 1, further including the step of separating the nucleic acid component of the sample from a solid component of the sample.

15. The method of claim 14, wherein the nucleic acid component is separated from the solid component by directing the fluid and the nucleic acid component through a mesh, whereby the solid component is retained by the mesh.

16. The method of claim 1, wherein the sample is a liquid.

17. The method of claim 1, wherein the sample is a slurry.

18. The method of claim 1, wherein the sample is a gas or an aerosol.

19. The method of claim 1, wherein the sample is a solid material or a wipe of a solid material.

20. The method of claim 1, wherein water is directed through the porous support by means of a pressure gradient.

21. The method of claim 1, wherein the water is directed through the porous support by mechanical means.

22. The method of claim 1, wherein the nucleic acid component includes DNA or a DNA fragment.

23. The method of claim 1, wherein the nucleic acid component includes RNA or a RNA fragment.

24. The method of claim 1, wherein the nucleic acid amplification inhibitor component includes at least one polymerase chain reaction inhibitor.

25. The method of claim 1, wherein the porous support binds polymerase chain reaction inhibitors in the sample.

26. The method of claim 1, wherein the porous support binds the nucleic acid amplification inhibitor component.

27. The method of claim 1, wherein said sample is collected directly onto the porous support by contacting the sample with the porous support that deactivates a nucleic acid amplification inhibitor component of the sample.

28. An apparatus for preparing a nucleic acid component of a sample for amplification, comprising:
   a) a porous support including an agent that deactivates a nucleic acid amplification inhibitor component of a sample contacting the porous support; and
   b) a housing having an opening and defining an interior, said interior being in fluid communication with the porous support, whereby at least a portion of a fluid directed through the opening is directed through at least a portion of the porous support and separates at least a portion of a nucleic acid component of a sample contacting the porous support from the support and from said nucleic acid amplification inhibitor component at the porous support, whereby deactivated components of the nucleic acid amplification inhibitor component are retained by the porous support or are soluble fragments that do not interfere with nucleic acid amplification procedures, thereby preparing the nucleic acid component for amplification.

29. The apparatus of claim 28, wherein the porous support is in interfering relation with flow of fluid directed through the opening of the housing.

30. The apparatus of claim 29, wherein the porous support is fixed at said opening.

31. The apparatus of claim 30, wherein said housing is elongate and defines the opening at a first end of the housing.

32. The apparatus of claim 31, wherein the housing is sealed at a second end.

33. The apparatus of claim 31, wherein a second end of the housing is sealed by a cap.

34. The apparatus of claim 33, wherein the cap is removable.

35. The apparatus of claim 33, wherein the cap defines a cap interior partitioned from the housing interior.

36. The apparatus of claim 35, wherein the cap further includes a means for directing a fluid from the cap interior into the housing interior.

37. The apparatus of claim 36, wherein said means includes an elongate conduit that extends from the cap interior into the housing interior.

38. The apparatus of claim 31, further including means for directing fluid through the opening into the housing interior.

39. The apparatus of claim 38, wherein the means for directing fluid into the housing interior include a fluid container, said fluid container having a shape that conforms with an exterior surface of the housing, whereby said housing can be aligned with the fluid container at the housing opening and directed into the fluid container, thereby directing fluid in the fluid container through the opening of the housing and into the housing, at least a portion of said fluid being directed through at least a portion of the porous support.

40. The apparatus of claim 39, wherein the fluid container is a multiple cartridge cassette.

41. The apparatus of claim 30, further including a desalting membrane between the porous support and the housing interior.

42. The apparatus of claim 41, further including a compression barrier between the desalting membrane and said housing interior.

43. The apparatus of claim 41, further including a membrane that removes proteins from the sample.

44. The apparatus of claim 41, further including a retaining ring at the opening.

45. The apparatus of claim 44, further including a mesh between the retaining ring and the porous support.

46. The apparatus of claim 28, wherein the housing defines a sample well and a plurality of wells in fluid communication with the sample well, and further including at least one valve at the sample well that selectively provides fluid communication between the sample well and at least one of said plurality of wells.

47. The apparatus of claim 28, wherein the agent further kills or lyses cells or spores in the sample.

48. The apparatus of claim 28, wherein the agent further deactivates DNases or RNases in the sample.

49. The apparatus of claim 28, wherein the porous support binds the nucleic acid amplification inhibitor component.

50. An apparatus for preparing a nucleic acid component of a sample for amplification, comprising:
   a) a sample chamber;
   b) a porous support that deactivates a nucleic acid amplification inhibitor component within the sample chamber, wherein the porous support includes a deactivating agent that deactivates the nucleic acid amplification inhibitor component of the sample, wherein the deactivated components of the nucleic acid amplification inhibitor component are retained by the porous support or are soluble fragments that do not interfere with nucleic acid amplification procedures; and
   c) means for directing liquid through the porous support in the sample chamber.

51. The apparatus of claim 50, further including at least one reagent chamber that is in fluid communication with the sample chamber.

52. The apparatus of claim 51, wherein the at least one reagent chamber is connected to the sample chamber via a conduit.

53. The apparatus of claim 52, wherein the porous support that deactivates a nucleic acid amplification inhibitor component is at a first end of the sample chamber.

54. The apparatus of claim 50, wherein the porous support binds the nucleic acid amplification inhibitor component.

55. A housing for extracting a nucleic acid component from a sample comprising:
   a) a tube having a first end and a second end;
   b) a chemically-treated porous support, the porous support including a deactivating agent that deactivates a nucleic acid amplification inhibitor component in the sample at the first end, wherein the deactivated components of the nucleic acid amplification inhibitor component are retained by the porous support or are soluble fragments that do not interfere with nucleic acid amplification procedures; and
   c) means for retaining the porous support that deactivates a nucleic acid amplification inhibitor component at the second end.

56. The housing of claim 55, further including a cap at the second end.

57. The housing of claim 56, wherein the cap is a removable cap.

58. The housing of claim 55, wherein the means for retaining the porous support is a retaining ring.

59. The housing of claim 55, further comprising a mesh positioned between the porous support and the means for retaining the porous support.

60. The housing of claim 55, further comprising at least one desalting membrane positioned at a porous support side facing the tube interior.

61. The housing of claim 60, wherein at least one desalting membrane is positioned between the porous support and a compression barrier.

62. The housing of claim 55, wherein the tube is fabricated from an inert material.

63. The housing of claim 62, wherein the inert material includes a plastic material.

64. The housing of claim 55, further comprising means for providing an electric field to detach the nucleic acid component from the porous support.

* * * * *